(12) United States Patent
Li

(10) Patent No.: US 10,080,494 B2
(45) Date of Patent: Sep. 25, 2018

(54) EYE LENS AND CORNEA MONITORING SYSTEM USING THE SAME

(71) Applicant: HON HAI PRECISION INDUSTRY CO., LTD., New Taipei (TW)

(72) Inventor: Wen-Kai Li, New Taipei (TW)

(73) Assignee: HON HAI PRECISION INDUSTRY CO., LTD., New Taipei (TW)

( * ) Notice: Subject to any disclaimer, the term of this patent is extended or adjusted under 35 U.S.C. 154(b) by 0 days.

(21) Appl. No.: 15/473,804

(22) Filed: Mar. 30, 2017

(65) Prior Publication Data
US 2017/0332900 A1  Nov. 23, 2017

(30) Foreign Application Priority Data
May 18, 2016  (TW) .............. 105115293 A

(51) Int. Cl.
| | |
|---|---|
| *A61B 3/00* | (2006.01) |
| *A61B 3/107* | (2006.01) |
| *G02C 11/00* | (2006.01) |
| *A61B 5/00* | (2006.01) |
| *G02C 7/04* | (2006.01) |

(52) U.S. Cl.
CPC ............ *A61B 3/107* (2013.01); *A61B 5/6821* (2013.01); *G02C 7/04* (2013.01); *G02C 11/10* (2013.01)

(58) Field of Classification Search
CPC ....... A61B 3/125; A61B 3/117; A61B 3/1015; A61B 3/14; A61B 3/13; G02C 7/04
USPC .................................................. 351/200–246
See application file for complete search history.

(56) References Cited

U.S. PATENT DOCUMENTS

| | | | | |
|---|---|---|---|---|
| 5,751,260 | A * | 5/1998 | Nappi ..................... | G06F 3/013 340/4.13 |
| 2015/0215601 | A1* | 7/2015 | Zhou .................... | H04N 13/042 348/43 |
| 2016/0070038 | A1* | 3/2016 | Peyman ................. | G02B 3/14 359/666 |

* cited by examiner

*Primary Examiner* — Mohammed Hasan
(74) *Attorney, Agent, or Firm* — ScienBiziP, P.C.

(57) ABSTRACT

An eye lens worn on a user's cornea monitors deformations of the cornea. The eye lens includes a substrate and at least one deformation sensor secured to the substrate. The deformation sensor is configured to monitor the curvature of cornea and any deformations, convert the deformations into digital signals, and transmit the digital signals out. A cornea monitoring system using the eye lens is also provided.

16 Claims, 3 Drawing Sheets

EYE LENS AND CORNEA MONITORING SYSTEM USING THE SAME

FIELD

The subject matter generally relates to an eye lens, and a cornea monitoring system using the eye lens.

BACKGROUND

A cornea is a transparent film in front of an eyeball that covers the iris, pupil, and anterior chamber. The cornea provides most of refractive power to the eye. A cornea with high transparency and appropriate refractive power can allow a clear image. The refractive power of the cornea mainly depends on the corneal curvature. A deformation of the cornea can lead to a change in corneal curvature. A small corneal curvature can lead to high refractive power and shortsightedness. If the deformation of the cornea can be monitored instantaneously, the change of the corneal curvature can be predicted in advance, thus allowing immediate measures to be taken to prevent the user from shortsightedness or myopia.

BRIEF DESCRIPTION OF THE DRAWINGS

Implementations of the present technology will now be described, by way of example only, with reference to the attached figures.

DETAILED DESCRIPTION

Figure 1:
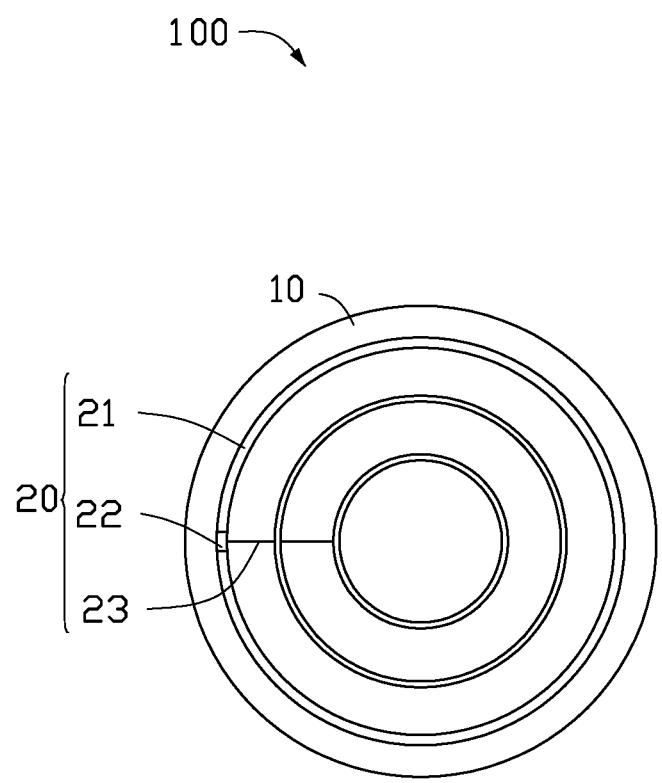
FIG. 1 is a diagrammatic view of an eye lens according to an exemplary embodiment of the present application.

It will be appreciated that for simplicity and clarity of illustration, where appropriate, reference numerals have been repeated among the different figures to indicate corresponding or analogous elements. In addition, numerous specific details are set forth in order to provide a thorough understanding of the exemplary embodiments described herein. However, it will be understood by those of ordinary skill in the art that the exemplary embodiments described herein can be practiced without these specific details. In other instances, methods, procedures, and components have not been described in detail so as not to obscure the related relevant feature being described. Also, the description is not to be considered as limiting the scope of the embodiments described herein. The drawings are not necessarily to scale and the proportions of certain parts may be exaggerated to better illustrate details and features of the present disclosure.

The term "comprising" when utilized, means "including, but not necessarily limited to"; it specifically indicates open-ended inclusion or membership in the so-described combination, group, series, and the like.

FIG. 1 illustrates an exemplary embodiment of an eye lens 100 configured to be worn on a user's cornea. The eye lens 100 provides monitoring of deformations of the cornea. The eye lens 100 includes a substrate 10 and at least one deformation sensor 20 secured to the substrate 10. The deformation sensor 20 is configured to monitor deformations of the cornea, convert the deformations into digital signals, and transmit the digital signals from the eye lens 100 to an external device, such as a signal processor or hub (not explicitly shown in FIG. 1).

The shape of the substrate 10 is the same as the shape of the user's cornea, and the substrate 10 can cover the user's cornea completely.

The eye lens 100 may be a hydrogel lens or a silicone hydrogel lens. When the eye lens 100 is hydrogel lens, the material of the substrate 10 is hydrogel matrix. When the eye lens 100 is silicone hydrogel lens, the material of the substrate 10 is silicone hydrogel matrix. The hydrogel matrix may be prepared by irradiating a hydrogel precursor with ultraviolet light (UV) to copolymerize the hydrogel precursor. The hydrogel precursor includes a hydrated polymer, a photoinitiator, and a cross-linking agent. The silicone hydrogel matrix may be prepared by irradiating a silicone hydrogel precursor with UV to copolymerize the silicone hydrogel precursor. The silicone hydrogel precursor includes a hydrated polymer, a photoinitiator, and a cross-linking agent.

When the material of the substrate 10 is hydrogel matrix, the hydrated polymer may be selected from a group consisting of methyl methacrylate (MMA) and hydroxyethyl methacrylate (HEMA). When the material of the substrate 10 is silicone hydrogel matrix, the hydrated polymer may be selected from a group consisting of MMA, HEMA, polydimethylsiloxane (PDMS), and tris(hydroxymethyl)aminomethane (TRIS).

The photoinitiator may be obtained from Chemical Industries Basel (CIBA) Corporation as a clear liquid under the trade name "Irgacure-1173". The cross-linking agent may be ethyleneglycol dimethacrylate (EGDMA).

The hydrogel precursor and silicone hydrogel precursor may further include a hydrophilic monomer. The hydrophilic monomer improves the water-affinity and oxygen permeability of the hydrogel matrix and the silicone hydrogel matrix. When the material of the substrate 10 is a hydrogel matrix, the hydrophilic monomer may be selected from a group consisting of N-Vinyl-2-pyrrolidone (NVP), glycidyl methacrylate (GMA), and N,N-Dimethylacrylamide (DMA). When the material of the substrate 10 is a silicone hydrogel matrix, the hydrophilic monomer may be N-Vinyl-2-pyrrolidone (NVP).

The deformation sensor 20 includes at least one sensing element 21, an integrated circuit chip 22, and at least one flexible wire 23. The sensing element 21 is electrically connected with the integrated circuit chip 22 through the wire 23. The sensing element 21 is configured to sense the deformation of the cornea, convert the deformation into analog signal, and then transmit the analog signal to the integrated circuit chip 22 through the wire 23. The integrated circuit chip 22 is configured to amplify the analog signal and convert the analog signal to digital signal, and then transmit the digital signal to an external device, such as a signal processor or hub (not explicitly shown in FIG. 1).

In one exemplary embodiment, the sensing element 21 is arranged on the surface of the substrate 10 in contact with the cornea. In another exemplary embodiment, the sensing element 21 is embedded inside of the substrate 10.

In one exemplary embodiment, the integrated circuit chip 22 and the wire 23 are arranged on the surface of the substrate 10. In another exemplary embodiment, the integrated circuit chip 22 and the wire 23 are embedded inside of the substrate 10. In one exemplary embodiment, the integrated circuit chip 22 is installed toward the edge of the substrate 10.

The sensing element 21 can be a flake-type sensing element or an annular sensing element. When the sensing element 21 is a flake-type sensing element, the deformation sensor 20 includes a plurality of flake sensing elements, and the plurality of flake sensing elements are scattered in the substrate 10. When the sensing element 21 is an annular sensing element, the central axis of the annular sensing element, the central axis of the eye lens 100, and the central axis of the cornea coincide with one another. When the deformation sensor 20 includes a plurality of annular sensing elements, each of the plurality of annular sensing elements has different radii, and the plurality of annular sensing elements are arranged on the substrate 10 in the form of concentric rings.

Figure 2:
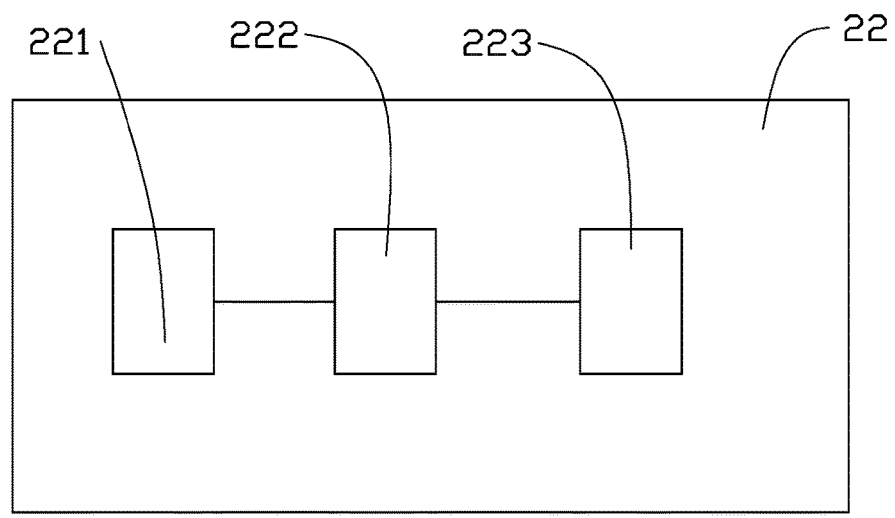
FIG. 2 is a diagrammatic view of an integrated circuit chip included in the eye lens of FIG. 1 according to an exemplary embodiment of the present application.

Referring to FIG. 2, the integrated circuit chip 22 includes a front end analog signal amplifier 221, a central processor 222 electrically connected with the front end analog signal amplifier 221, and an antenna 223 electrically connected with the central processor 222. The antenna 223 is configured to receive and transmit signals. The antenna 223 is also configured to receive electric energy through electromagnetic coupling effect.

The sensing element 21 electrically connects with the front end analog signal amplifier 221 through the wire 23. The sensing element 21 transmits the analog signal of the deformation of cornea to the front end analog signal amplifier 221 through the wire 23. The front end analog signal amplifier 221 buffers and amplifies the analog signal, and then transmits the analog signal to the central processor 222. The central processor 222 converts the analog signal to digital signal, and then stores the digital signal. The antenna 223 transmits the digital signal wirelessly to an external device, such as a signal processor or hub (not explicitly shown in FIG. 2).

The integrated circuit chip 22 includes silicon substrate. The outer surface of the integrated circuit chip 22 is wrapped by a biocompatible polymer film. The outer surface of the sensing element 21 and the wire 23 can also be wrapped by biocompatible polymer film.

The eye lens 100 can have degrees of optical bias, thereby the eye lens 100 can be worn by nearsighted and farsighted people. The eye lens 100 can also have no degree of optical bias, thereby the eye lens 100 can be worn by people who are not nearsighted or farsighted.

Figure 3:
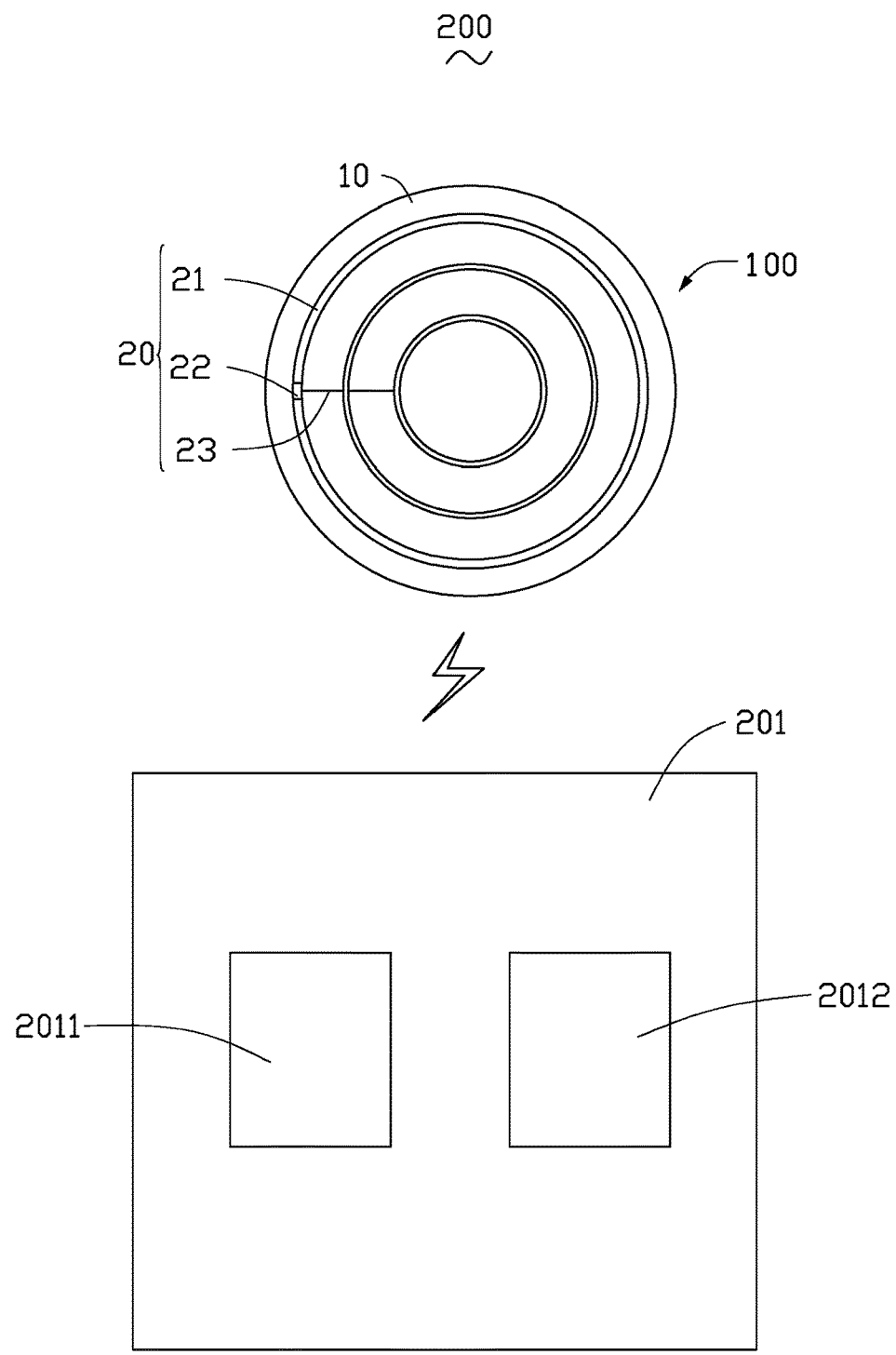
FIG. 3 is a diagrammatic view of a cornea monitoring system according to an exemplary embodiment of the present application.

FIG. 3 illustrates an exemplary embodiment of a cornea monitoring system 200 including the eye lens 100 and a signal processor 201. The signal processor 201 is configured to receive digital signal transmitted from the deformation sensor 20 of the eye lens 100, then analyze and fit the digital signal to achieve numerical value of the corneal curvature, then store and reveal the numerical value for users, optometrists, or doctors to check. When the corneal curvature is out of the normal range, timely treatment measures can be taken.

The signal processor 201 includes a wireless signal receiving and processing unit 2011 and a display 2012.

The signal processor 201 can be computer or smart bracelet with wireless signal receiving and processing functions.

The exemplary embodiments shown and described above are only examples. Even though numerous characteristics and advantages of the present technology have been set forth in the foregoing description, together with details of the structures and function of the present disclosure, the disclosure is illustrative only, and changes can be made in the detail, including in matters of shape, size, and arrangement of the parts within the principles of the present disclosure, up to and including the full extent established by the broad general meaning of the terms used in the claims.

What is claimed is:

1. An eye lens comprising:
   a substrate; and
   a deformation sensor secured to the substrate;
   wherein the deformation sensor is configured to instantaneously monitor a deformation of a cornea, convert the deformation into a digital signal, and transmit the digital signal out of the eye lens;
   the deformation sensor includes at least one sensing element, an integrated circuit chip and at least one wire, the at least one sensing element is electrically connected to the integrated circuit chip through the at least one wire, the at least one sensing element is configured to sense the deformation of the cornea, convert the deformation into an analog signal, and transmit the analog signal to the integrated circuit chip; the integrated circuit chip is configured to amplify the analog signal and convert the analog signal to the digital signal, and transmit the digital signal out;
   the integrated circuit chip includes a front end analog signal amplifier, a central processor electrically connected to the front end analog signal amplifier, and an antenna electrically connected to the central processor, the antenna is configured to receive and transmit energy and signal, the at least one sensing element electrically connects with the front end analog signal amplifier through the at least one wire, the at least one sensing element is configured to transmit the analog signal of the deformation of the cornea to the front end analog signal amplifier through the at least one wire; the front end analog signal amplifier is configured to buffer and amplify the analog signal, and then transmit the analog signal to the central processor; the central processor is configured to convert the analog signal to the digital signal, and store the digital signal; the antenna is configured to transmit the digital signal out wirelessly.

2. The eye lens of claim 1, wherein the at least one sensing element is arranged on a surface of the substrate in contact with the cornea.

3. The eye lens of claim 1, wherein the at least one sensing element is embedded inside of the substrate.

4. The eye lens of claim 1, wherein the at least one sensing element is a flake-type sensing element.

5. The eye lens of claim 1, wherein the at least one sensing element is an annular sensing element, wherein a central axis of the annular sensing element and a central axis of the eye lens coincide with each other.

6. The eye lens of claim 5, wherein the deformation sensor comprises a plurality of annular sensing elements, the plurality of annular sensing elements have different radii, and the plurality of annular sensing elements are arranged on the substrate in concentric rings.

7. The eye lens of claim 1, wherein the integrated circuit chip is wrapped by a biocompatible polymer film.

8. The eye lens of claim 1, wherein the at least one sensing element and the at least one wire are wrapped by a biocompatible polymer film.

9. A cornea monitoring system comprising:
   a signal processor; and
   an eye lens comprising:
      a substrate; and
      a deformation sensor secured to the substrate;
   wherein the deformation sensor is configured to instantaneously monitor a deformation of cornea, convert the deformation into a digital signal, and transmit the digital signal out of the eye lens;

the deformation sensor includes at least one sensing element, an integrated circuit chip and at least one wire, the at least one sensing element is electrically connected to the integrated circuit chip through the at least one wire, the at least one sensing element is configured to sense the deformation of the cornea, convert the deformation into an analog signal, and transmit the analog signal to the integrated circuit chip; the integrated circuit chip is configured to amplify the analog signal and convert the analog signal to the digital signal, and transmit the digital signal out;

the integrated circuit chip includes a front end analog signal amplifier, a central processor electrically connected to the front end analog signal amplifier, and an antenna electrically connected to the central processor, the antenna is configured to receive and transmit energy and signal, the at least one sensing element electrically connects with the front end analog signal amplifier through the at least one wire, the at least one sensing element is configured to transmit the analog signal of the deformation of the cornea to the front end analog signal amplifier through the at least one wire; the front end analog signal amplifier is configured to buffer and amplify the analog signal, and then transmit the analog signal to the central processor; the central processor is configured to convert the analog signal to the digital signal, and store the digital signal; the antenna is configured to transmit the digital signal out wirelessly.

10. The cornea monitoring system of claim 9, wherein the at least one sensing element is arranged on a surface of the substrate in contact with the cornea.

11. The cornea monitoring system of claim 9, wherein the at least one sensing element is embedded inside of the substrate.

12. The cornea monitoring system of claim 9, wherein the at least one sensing element is a flake-type sensing element.

13. The cornea monitoring system of claim 9, wherein the at least one sensing element is an annular sensing element, wherein a central axis of the annular sensing element and a central axis of the eye lens coincide with each other.

14. The cornea monitoring system of claim 13, wherein the deformation sensor comprises a plurality of annular sensing elements, the plurality of annular sensing elements have different radii, and the plurality of annular sensing elements are arranged on the substrate in concentric rings.

15. The cornea monitoring system of claim 9, wherein the integrated circuit chip is wrapped by a biocompatible polymer film.

16. The cornea monitoring system claim 9, wherein the at least one sensing element and the at least one wire are wrapped by a biocompatible polymer film.

* * * * *